(12) United States Patent
Jung et al.

(10) Patent No.: US 11,426,571 B2
(45) Date of Patent: Aug. 30, 2022

(54) MICRONEEDLE ARRAY WITH COMPOSITE FORMULATION, AND METHOD FOR MANUFACTURING SAME

(71) Applicant: INDUSTRY-ACADEMIC COOPERATION FOUNDATION, YONSEI UNIVERSITY, Seoul (KR)

(72) Inventors: Hyung Il Jung, Seoul (KR); Hui Suk Yang, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 207 days.

(21) Appl. No.: 16/462,120

(22) PCT Filed: Nov. 20, 2017

(86) PCT No.: PCT/KR2017/013193
§ 371 (c)(1),
(2) Date: Sep. 23, 2019

(87) PCT Pub. No.: WO2018/093218
PCT Pub. Date: May 24, 2018

(65) Prior Publication Data
US 2020/0016388 A1 Jan. 16, 2020

(30) Foreign Application Priority Data
Nov. 18, 2016 (KR) .................. 10-2016-0154036

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61M 2037/0023* (2013.01); *A61M 2037/0053* (2013.01)

(58) Field of Classification Search
CPC ...... A61M 37/0015; A61M 2037/0023; A61M 2037/0053; A61M 2037/0046; A61K 9/0021; A61K 47/36; A61K 9/06
See application file for complete search history.

(56) References Cited

U.S. PATENT DOCUMENTS

2002/0020688 A1* 2/2002 Sherman ................ B29C 51/00
216/2
2002/0061336 A1* 5/2002 O'Connor ............ A61K 9/1652
424/499

(Continued)

FOREIGN PATENT DOCUMENTS

KR      2015-0138646     12/2015
WO      WO 2015/164840   10/2015

OTHER PUBLICATIONS

International Search Report and Written Opinion issued in Corresponding International Patent Application No. PCT/KR2017/013193, dated Mar. 19, 2018 (English Translation).

*Primary Examiner* — Amber R Stiles
(74) *Attorney, Agent, or Firm* — Norton Rose Fulbright US LLP (57) ABSTRACT

The present invention relates to a microneedle array and a method for manufacturing the same, the microneedle array comprising: a support; and a plurality of microneedles loaded with a solid-phase formulation which protrude from the upper portion of the support, wherein a liquid-phase formulation is applied or added dropwise onto an area of the upper portion of the support in which the microneedles are not formed, or in a case where one or more holes are formed in the support, the liquid-phase formulation is released, through the holes, onto the area of the upper portion of the support in which the microneedles are not formed.

12 Claims, 7 Drawing Sheets

(56) References Cited

U.S. PATENT DOCUMENTS

| | | | |
|---|---|---|---|
| 2002/0193729 A1* | 12/2002 | Cormier | A61M 37/0015 604/46 |
| 2006/0024358 A1 | 2/2006 | Santini et al. | |
| 2007/0250018 A1 | 10/2007 | Adachi et al. | |
| 2008/0125743 A1 | 5/2008 | Yuzhakov | |
| 2008/0269685 A1* | 10/2008 | Singh | A61K 38/385 604/173 |
| 2011/0112509 A1* | 5/2011 | Nozaki | A61M 37/0015 604/173 |
| 2012/0041337 A1* | 2/2012 | Ferguson | A61M 37/0015 600/573 |
| 2013/0041330 A1* | 2/2013 | Matsudo | A61K 9/0021 604/272 |
| 2013/0165872 A1 | 6/2013 | Stumber | |

\* cited by examiner

MICRONEEDLE ARRAY WITH COMPOSITE FORMULATION, AND METHOD FOR MANUFACTURING SAME

Cross-Reference to Related Applications

This application is a national phase application under 35 U.S.C. § 371 of International Application No. PCT/KR2017/013193, filed Nov. 20, 2017, which claims priority to and the benefit of Korean Patent Application No. 10-2016-0154036, filed Nov. 18, 2016. The contents of the referenced patent applications are incorporated into the present application by reference.

TECHNICAL FIELD

The present invention relates to a microneedle array with a composite formulation, and a method for manufacturing the same.

BACKGROUND ART

A subcutaneous drug injection method is one of the methods commonly used for treatment of various diseases and drug delivery. The subcutaneous drug injection method has advantages such as having low drug denaturation and degradation rates, high drug delivery efficiency in the body, and decreased side effects due to delivery of a predetermined amount of drug, as compared with an oral drug delivery method in which a drug is absorbed while passing through the body's digestive organs. Currently, hypodermic needles having various diameters are widely used for the subcutaneous drug injection method.

Conventional hypodermic needles are used in most drug delivery methods. However, when a hypodermic needle is inserted into the skin, skin damage and occurrence of pain are inevitable depending on the length and diameter of the hypodermic needle, and side effects such as occurrence of an allergic reaction due to a metallic material and occurrence of needle phobia due to pain occur. In particular, in a case of a specific disease which requires repetitive drug injections for a short period of time, it is not possible to perform injection at the same site due to a wound caused by use of conventional subcutaneous injection, and there are problems such as decreased patient convenience and decreased drug injection efficiency.

In order to solve the problems with conventional hypodermic needles, a microneedle which allows subcutaneous drug injection in micro size has been developed. The microneedle is a micro-sized structure that can solve the problems with conventional hypodermic needles such as pain, trauma, and decreased patient convenience; and biodegradable microneedle technologies, which allow drugs to be delivered in a minimally invasive and painless manner, are a field of research that recently attracts attention.

On the other hand, the microneedle is a 'patch' formulation to be attached to the skin, and performs a drug delivery action of injection without any pain. Thus, the microneedle can newly deliver drugs that cannot be delivered by conventional patch types. Conventional microneedles were attached on the skin, along with a patch, in a form arranged on a support. Therefore, in order to apply an additional formulation such as a cream formulation, a method of applying the same to the skin before or after application of microneedles was used. However, for such an application method, a process of applying a separate additional formulation is required, and there is a limitation that a patch must remain attached until the patch is attached and all microneedles are absorbed, during which application of an additional formulation is not possible. In addition, because microneedles form micropores that pass through the skin, there may be cases where additional processes, such as performing disinfection before application of a microneedle patch and applying skin layer restoration cream after application of the microneedle patch, are required, which causes problems that side effects may occur in a case where processes in question are not performed due to ease of use and the user's carelessness.

Technical Problem

In order to diversify and maximize efficacy of a microneedle array, the present invention intends to provide a microneedle array and the like, the microneedle array comprising: a support; and a plurality microneedles loaded with a solid-phase formulation material which protrude from the upper portion of the support, wherein a liquid-phase formulation material is applied or added dropwise onto an area of the upper portion of the support in which the microneedle is not formed, or in a case where one or more holes are formed in the support, the liquid-phase formulation material is released, through the holes, onto the area of the upper portion of the support in which the microneedle is not formed.

However, the technical problem to be solved by the present invention is not limited to the above-mentioned problems, and other problems not mentioned can be clearly understood by those skilled in the art from the following description.

Solution to Problem

The present invention provides a microneedle array and the like, the microneedle array comprising: a support; and a plurality microneedles loaded with a solid-phase formulation material which protrude from the upper portion of the support, wherein a liquid-phase formulation material is applied or added dropwise onto an area of the upper portion of the support in which the microneedle is not formed, or in a case where one or more holes are formed in the support, the liquid-phase formulation material is released, through the holes, onto the area of the upper portion of the support in which the microneedle is not formed.

The microneedle may be loaded with two or more solid-phase forming materials to form a multi-layer structure.

A type of the liquid-phase formulation material may be the same as or different from that of the solid-phase formulation material.

In a case where the type of the liquid-phase formulation material is different from that of the solid-phase formulation material, the liquid-phase formulation material may contain a fat-soluble material including one or more selected from the group consisting of horse oil, vitamin A and a derivative thereof, vitamin D and a derivative thereof, vitamin E and a derivative thereof, vitamin K and a derivative thereof, organic sunscreen, and a fat-soluble plant extract; or a water-soluble material including one or more selected from the group consisting of vitamin B and a derivative thereof, vitamin C and a derivative thereof, epigallocatechin gallate, a water-soluble plant extract, a water-soluble flavor, an enzyme, a microbial extract, and a mineral.

In a case where the type of the liquid-phase formulation material is different from that of the solid-phase formulation material, the liquid-phase formulation material may contain a material for dissolving the microneedles when the microneedles are applied to the human body.

In a case where the type of the liquid-phase formulation material is different from that of the solid-phase formulation material, the liquid-phase formulation material may contain a material for protecting the skin from the microneedles when the microneedles are applied to the human body.

The liquid-phase formulation material may be encapsulated.

The microneedle array may further comprise pressurizing means for releasing the liquid-phase formulation material.

The microneedle array may further comprise an adhesive layer formed on the lower portion of the support.

In an embodiment of the present invention, there is provided a method for manufacturing a microneedle array, comprising: (a) a step of preparing a support; (b) a step of forming, on the upper portion of the support, a plurality of microneedles loaded with a solid-phase formulation material which protrude from the upper portion; and (c) a step of applying or adding dropwise a liquid-phase formulation material onto an area of the upper portion of the support in which the microneedle is not formed.

In another embodiment of the present invention, there is provided a method for manufacturing a microneedle array, comprising: (a) a step of preparing a support having one or more holes formed therein; (b) a step of forming, on the upper portion of the support, a plurality of microneedles loaded with a solid-phase formulation material which protrude from the upper portion; and (c) a step of releasing a liquid-phase formulation material, through the holes, onto an area of the upper portion of the support in which the microneedle is not formed.

The method may further comprise, before or after the step (b), a step of injecting the liquid-phase formulation material so as to be positioned in the lower portion or the inside of the support.

In the step (b), the microneedles may be obtained by placing a plurality of viscous compositions on the upper portion of the support, and then performing molding and curing thereof.

Advantageous Effects of Invention

The microneedle array with a composite formulation according to the present invention is characterized by comprising: a support; and a plurality microneedles loaded with a solid-phase formulation material which protrude from the upper portion of the support, wherein a liquid-phase formulation material is applied or added dropwise onto an area of the upper portion of the support in which the microneedle is not formed, or in a case where one or more holes are formed in the support, the liquid-phase formulation material is released, through the holes, onto the area of the upper portion of the support in which the microneedle is not formed. Thus, the solid-phase formulation material loaded on the microneedle and the liquid-phase formulation material can be simultaneously delivered into the body (transdermally, mucosally, or the like), thereby diversifying efficacy; and, in addition, the solid-phase formulation material loaded on the microneedle and the liquid-phase formulation material can interact with each other to regulate a rate at which the microneedle is dissolved in the body, thereby maximizing efficacy.

Furthermore, the liquid-phase formulation material allows materials, which are difficult to be loaded on conventional viscous compositions for manufacturing microneedles, to be contained, which provides an advantage that such materials can also be effectively delivered into the body. In addition, a material for dissolving the microneedles may be contained in the liquid-phase formulation material, which provides an advantage that a dissolution rate of the solid-phase formulation material loaded on the microneedle can be regulated when the microneedles are applied to the human body with the liquid-phase formulation material. In addition, when the microneedles are applied to the human body with the liquid-phase formulation material, an advantage that a material for protecting the skin from the microneedle can be contained in the liquid-phase formulation material is provided.

DETAILED DESCRIPTION OF INVENTION

Conventionally, it is common to apply a liquid-phase formulation material for disinfection or the like before use of a microneedle array, or to apply a liquid-phase formulation material for skin restoration or the like after use of the microneedle array. In such cases, there is a limitation that dissolution of microneedles in the body is not only inefficient but also the liquid-phase formulation material is not simultaneously applied during a process in which the microneedles are dissolved in the body. In order to overcome this limitation, the present inventors have manufactured a microneedle array with a composite formulation and have identified that this microneedle array has diversified and maximized efficacy, thereby completing the present invention.

As used herein, the term "microneedle array" refers to a system in which a plurality of microneedles protrude from the upper portion of a support.

As used herein, the term "microneedle" refers to a tool for delivering a material into the body (transdermally, mucosally, or the like). From the viewpoint that the microneedle has a pointed portion, the microneedle refers to a structure in which such a pointed portion forms a micropore that partially or entirely passes through the body surface (transdermally, mucosally, or the like) and a material is delivered through such a micropore. The microneedle may have various shapes including various effective lengths, diameters of tip and bottom of the pointed portion, and the like. Here, the term "effective length" refers to a vertical length from the tip of the pointed portion to the surface of a substrate, and may be 100 to 10,000 µm, 200 to 10,000 µm, 300 to 8,000 µm, or 500 to 2,000 µm. The term "tip of the pointed portion" refers to one end part of the pointed portion having the smallest diameter, and may have a diameter of 1 to 500 µm, 2 to 300 µm, or 5 to 100 µm. In addition, the term "bottom of the pointed portion" refers to one end part having the largest diameter, and may have a diameter of 50 to 1,000 µm.

Specifically, the microneedle can be classified into a solid-type microneedle and a hollow-type microneedle.

As used herein, the term "solid-phase formulation material" refers to a conventional solid-state material which has a certain shape and of which a shape or volume does easily change due to an external force or changes in pressure. Specifically, the solid-phase formulation material has a solid content of preferably 70% or more and more preferably 90% or more. However, the solid content is not limited thereto.

On the other hand, as used herein, the term "liquid-phase formulation material" has the opposite meaning of the solid-phase formulation material. The liquid-phase formulation material may refer to a material in a pure liquid state which does not have a certain shape and of which a shape changes, and may also refer to a material in a semi-solid or gel state which has a relatively certain shape and of which a shape relatively easily changes, as compared with the solid-phase formulation material, due to an external force or changes in pressure; that is, the liquid-phase formulation material is used in a broad concept that includes all materials in a liquid, semi-solid, or gel state.

Hereinafter, examples of the present invention will be described in detail with reference to the accompanying drawings so that those skilled in the art to which the present invention pertains can easily practice the present invention. The present invention may be embodied in many different forms and is not limited to the examples described herein.

In the drawings, thicknesses are enlarged to clearly represent several layers and areas. Also, in the drawings, for convenience of explanation, thicknesses of some layers and areas are exaggeratedly represented.

Hereinafter, formation of any configuration "on upper portion (or lower portion) of a substrate not only means that any configuration is formed in a state of being brought into contact with the upper portion (or the lower portion) of the substrate, but also does not have a restriction that other configurations are not included between the substrate and any configuration formed on the upper portion (or lower portion) of the substrate.

Hereinafter, the present invention will be described in detail.

Microneedle Array

A microneedle array according to an embodiment of the present invention comprises a support; and a plurality microneedles loaded with a solid-phase formulation material which protrude from the upper portion of the support, wherein a liquid-phase formulation material is applied or added dropwise onto an area of the upper portion of the support in which the microneedle is not formed.

Figure 1:
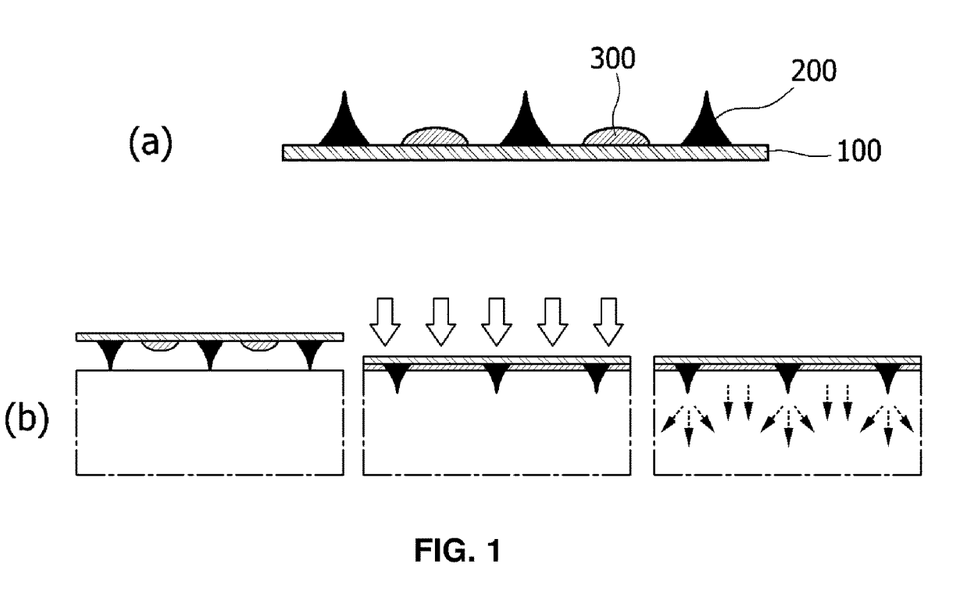
FIG. 1 illustrates views showing a microneedle array with a composite formulation according to an embodiment of the present invention, and a process of applying the same to the body.

FIG. 1(A) illustrates a view showing a microneedle array with a composite formulation according to an embodiment of the present invention, and FIG. 1(B) illustrates a view showing a process in which the microneedle array with a composite formulation according to the embodiment of the present invention is applied to the body.

As shown in FIG. 1(A), the microneedle array with a composite formulation according to the embodiment of the present invention comprises a support 100; and a plurality microneedles 200 loaded with a solid-phase formulation material which protrude from the upper portion of the support 100, wherein a liquid-phase formulation material 300 is applied or added dropwise onto an area of the upper portion of the support 100 in which the microneedle is not formed. Although not shown in the drawing, the microneedle array may further comprise an adhesive layer formed on the lower portion of the support 100.

A microneedle array according to another embodiment of the present invention is characterized by comprising: a support having one or more holes formed therein; and a plurality microneedles loaded with a solid-phase formulation material which protrude from the upper portion of the support, wherein a liquid-phase formulation material is released, through the holes, onto the area of the upper portion of the support in which the microneedle is not formed.

Figure 2:
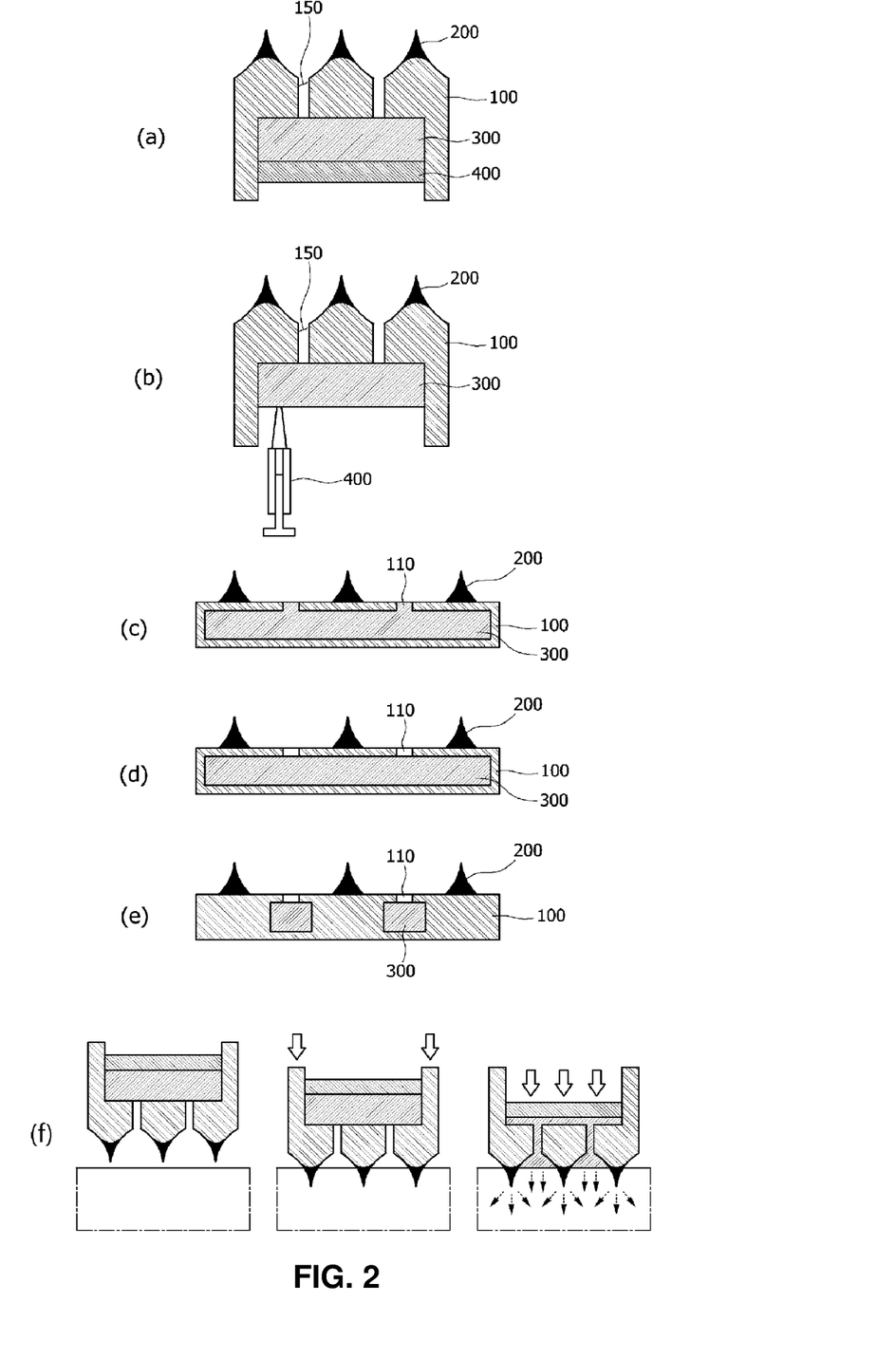
FIG. 2 illustrates views showing microneedle arrays with a composite formulation according to other embodiments of the present invention, and a process of applying the same to the body.

FIGS. 2(A) to 2(E) illustrate views showing microneedle arrays with a composite formulation according to other embodiments of the present invention, and FIG. 2(F) illustrates a view showing a process in which the microneedle array with a composite formulation according to the other embodiment of the present invention is applied to the body.

As illustrated in FIGS. 2(A) to 2(E), the microneedle array with a composite formulation according to the other embodiment of the present invention comprises a support 100 having one or more holes 150 formed therein; and a plurality microneedles 200 loaded with a solid-phase formulation material which protrude from the upper portion of the support 100, wherein a liquid-phase formulation material 300 is released, through the holes 150, onto the area of the upper portion of the support 100 in which the microneedle is not formed. Although not shown in the drawings, the microneedle array may further comprise an adhesive layer formed on the lower portion of the support 100.

Specifically, as illustrated in FIGS. 2(A) to 2(B), the microneedle array may further comprise pressurizing means 400 for releasing the liquid-phase formulation material. In addition, as illustrated in FIGS. 2(D) to 2(E), the microneedle array may further comprise a cap 110 for temporarily preventing the liquid-phase formulation material from being released early through the hole 150.

Accordingly, the solid-phase formulation material loaded on the microneedle 200 and the liquid-phase formulation material 300 can be simultaneously delivered into the body (transdermally, mucosally, or the like), thereby diversifying efficacy; and, in addition, the solid-phase formulation material loaded on the microneedle 200 and the liquid-phase formulation material 300 can interact with each other to regulate a rate at which the microneedle 200 is dissolved in the body, thereby maximizing efficacy.

First, the microneedle array with a composite formulation according to the present invention comprises a support 100.

Specifically, the support 100 serves to support a plurality of microneedles 200 loaded with a solid-phase formulation material. The support 100 may be formed in various structures such as a plate structure and a polyhedral structure having one or more inner hollow spaces.

In an embodiment, the support 100 may not have holes formed therein. In this case, the microneedle array is characterized in that the liquid-phase formulation material 300 is applied or added dropwise onto an area of the upper portion of the support 100 in which the microneedle 200 is not formed.

In another embodiment, the support 100 may have one or more holes 150 formed therein. In this case, the microneedle array is characterized in that the liquid-phase formulation material 300 is released, through the holes 150, onto the area of the upper portion of the support 100 in which the microneedle 200 is not formed. Specifically, in a case where the support 100 has a plate structure and has one or more holes 150 formed entirely through the support 100, the liquid-phase formulation material 300 may be injected to be positioned in the lower portion of the support 100. On the other hand, in a case where the support 100 has a polyhedral structure having one or more inner hollow spaces and has one or more holes 150 formed entirely through the upper surface of the support 100, the liquid-phase formulation material 300 may be injected to be positioned in the inside of the support 100. As the case may be, the microneedle array may further comprise a cap 110 for temporarily preventing the liquid-phase formulation material 300 from being released early through the hole 150. The cap 110 may be removed by detachment, discharge, rotation, dissolution, tearing, or the like thereof, before applying the liquid-phase formulation material 300 to the human body.

In addition, the support 100 may have various structures. The support 100 may have a single-layer or multi-layer structure, and may have a flat-plate structure or a structure in which a pillar region having various shapes is formed. The structure in which a pillar region is formed refers to a plate structure having a protruding or columnar shape. The pillar region has a cross-sectional shape such as a circle, a triangle, and a square, but the cross-sectional shape is not limited thereto.

FIG. 3(A) to 3(I) illustrate views showing various structures of the support in a microneedle array with a composite formulation according to an embodiment of the present invention.

Figure 3:
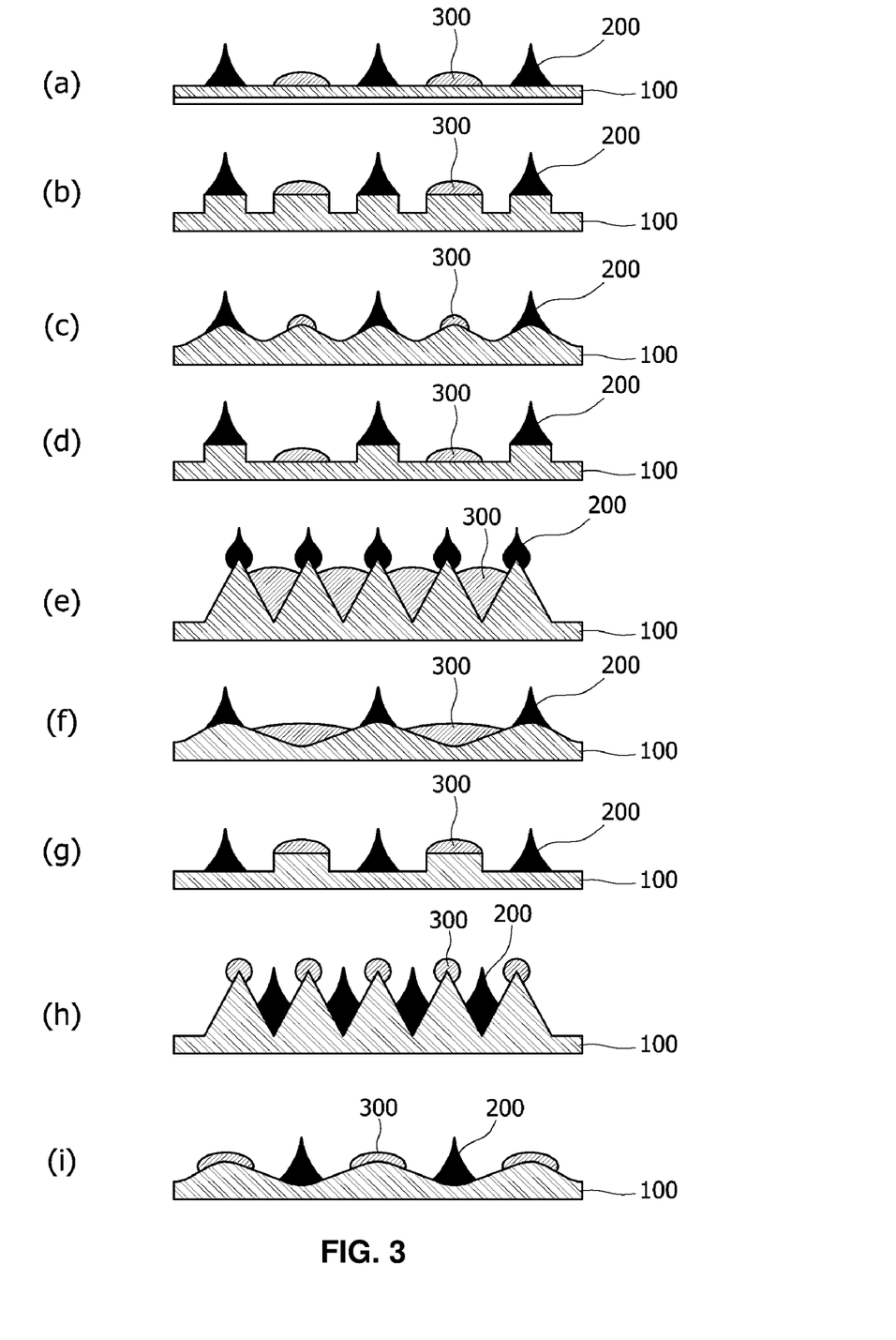
FIG. 3 illustrates views showing various structures of a support in a microneedle array with a composite formulation according to an embodiment of the present invention.

As illustrated in FIG. 3(A), the support 100 may have a multi-layer structure. As illustrated in FIGS. 3(B) and 3(C), the microneedle 200 and the liquid-phase formulation material 300 may be formed on a first pillar region and a second pillar region, respectively. As illustrated in FIGS. 3(D) and 3(F), the microneedle 200 may be formed on the pillar region and the liquid-phase formulation material 300 may be formed between the pillar regions. On the contrary, as illustrated in FIGS. 3(G) and 3(I), the microneedle 200 may be formed between the pillar regions and the liquid-phase formulation material 300 may be formed on the pillar region.

As such, a degree of interaction between the solid-phase formulation material loaded on the microneedle 200 and the liquid-phase formulation material 300 can be regulated by varying a structure of the support 100 and changing positions where the microneedle 200 and the liquid-phase formulation material 300 are formed, and a rate at which the microneedle 200 is dissolved in the body can be regulated through various implementations such as a penetration depth into the body and applied pressure. As a result, maximized efficacy can be exerted.

In addition, the support 100 may be formed of various materials. Specifically, the support may be formed of at least one material selected from the group consisting of a polymer material, a metal, ceramic, glass, a film, an adhesive patch, a vinyl-based material, silicone, a fiber sheet, nanofiber, and paper. However, the present invention is not limited thereto. Here, in a case where a material forming the support 100 consists of two or more types of materials, the material may be in a mixed form or in the form of divided layers. However, the present invention is not limited thereto.

In addition, the support 100 may have various properties depending on a specific type of the material. For example, in a case where the support 100 is formed of an elastic material, the support 100 may have a flexible shape, and thus the support 100 may have a changed shape depending on a degree of pressure at the time of being applied to the human body, by which a degree of interaction between the microneedle 200 and the liquid-phase formulation material 300 can also be regulated. On the other hand, in a case where the support 100 is formed of a fibrous material, the support 100 can partially absorb and store the liquid-phase formulation material 300, so that a degree of release of the liquid-phase formulation material 300 can also be regulated at the time of being applied to the human body.

Next, the microneedle array with a composite formulation according to the present invention comprises a plurality of microneedles 200 loaded with a solid phase formulation material. The microneedle 200 is characterized by protruding from the upper portion of the support 100.

Specifically, the microneedle 200 is loaded with a solid-phase formulation material. In a case where the microneedle 200 is a solid-type microneedle, the solid-phase formulation material may be a biocompatible or biodegradable material; in addition, the solid material may be a metallic material. Here, the biocompatible or biodegradable material has an advantage that it is eventually dissolved after penetration into the body; on the contrary, the metallic material is not dissolved after penetration into the body, and thus the metallic material needs to be separately removed.

The biocompatible material refers to a material which is substantially non-toxic to the human body, is chemically inert, and has no immunogenicity. The biodegradable material refers to a material which can be degraded in vivo by body fluids, microorganisms, or the like.

Here, as the biocompatible or biodegradable material, the following may be used: Hyaluronic acid, polyester, polyhydroxyalkanoate (PHA), poly($\alpha$-hydroxyacid), poly($\beta$-hydroxyacid), poly(3-hydroxybutyrate-co-valerate, PHBV), poly(3-hydroxypropionate, PHP), poly(3-hydroxyhexanoate, PHH), poly(4-hydroxyacid), poly(4-hydroxybutyrate), poly(4-hydroxyvalerate), poly(4-hydroxyhexanoate), poly (ester amide), polycaprolactone, polylactide, polyglycolide, poly(lactide-co-glycolide, PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazene, PHA-PEG, ethylene vynyl alcohol copolymer (EVOH), polyurethane, silicone, polyester, polyolefin, polyisobutylene and ethylene-alpha olefin copolymer, styrene-isobutylene-styrene triblock copolymer, acrylic polymer and copolymer, vinyl halide polymer and copolymer, polyvinyl chloride, polyvinyl ether, polyvinyl methyl ether, polyvinylidene halide, polyvinylidene fluoride, polyvinylidene chloride, polyfluoroalkene, polyperfluoroalkene, polyacrylonitrile, polyvinyl ketone, polyvinylaromatic, polystyrene, polyvinyl ester, polyvinyl acetate, ethylene-methyl methacrylate copolymer, acrylonitrile-styrene copolymer, ABS resin and ethylene-vinyl acetate copolymer, polyamide, alkyd resin, polyoxymethylene, polyimide, polyether, polyacrylate, polymethacrylate, polyacrylic acid-co-maleic acid, chitosan, dextran, cellulose, heparin, alginate, inulin, starch, or glycogen, with hyaluronic acid, polyester, polyhydroxyalkanoate (PHA), poly(α-hydroxyacid), poly(β-hydroxyacid), poly(3-hydroxybutyrate-co-valerate, PHBV), poly(3-hydroxypropionate, PHP), poly(3-hydroxyhexanoate, PHH), poly(4-hydroxyacid), poly(4-hydroxybutyrate), poly(4-hydroxyvalerate), poly(4-hydroxyhexanoate), poly(ester amide), polycaprolactone, polylactide, polyglycolide, poly(lactide-co-glycolide, PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphazene, PHA-PEG, chitosan, dextran, cellulose, heparin, alginate, inulin, starch, or glycogen being preferably used. However, the present invention is not limited thereto.

In a case where the microneedle 200 is a solid-type microneedle loaded with a biocompatible or biodegradable material, a drug may be additionally loaded thereon. The drug means a broad concept, and includes not only therapeutic agents for therapeutic purpose in a narrow sense but also energy, a nano component, a cosmetic ingredient (for example, a wrinkle improver, an anti-aging agent for skin, and a skin whitening agent), cell culture, and the like.

Specifically, the therapeutic agent includes a chemical drug, a protein/peptide medicament, a peptide medicament, a nucleic acid molecule for gene therapy, and the like.

For example, the therapeutic agent includes, but is not limited to, an anti-inflammatory agent, an analgesic agent, an antiarthritic agent, an antispasmodic agent, an antidepressant, an antipsychotic drug, a tranquilizer, an anxiolytic agent, a narcotic antagonist, an anti-parkinson's disease drug, a cholinergic agonist, an anticancer agent, an anti-angiogenic agent, an immunosuppressant, an anti-viral agent, antibiotics, an anorectic agent, an analgesic agent, an anticholinergic, an antihistamine, an anti-migraine agent, a hormone, a coronary, cerebrovascular, or peripheral vasodilator, a contraceptive, an antithrombotic agent, a diuretic, an antihypertensive agent, a therapeutic agent for cardiovascular diseases, and the like.

In particular, the protein/peptide medicament includes, but is not limited to, a hormone, a hormone analogue, an enzyme, an enzyme inhibitor, a signal transduction protein or a part thereof, an antibody or a part thereof, a single chain antibody, a binding protein or a binding domain thereof, an antigen, an adhesion protein, a structural protein, a regulatory protein, a toxin protein, a cytokine, a transcription regulatory factor, a blood coagulation factor, a vaccine, and the like. More specifically, the protein/peptide medicament may include insulin, insulin-like growth factor 1 (IGF-1), growth hormone, erythropoietin, granulocyte-colony stimulating factor (G-CSF), granulocyte/macrophage-colony stimulating factor (GM-CSF), interferon α, interferon β, interferon γ, interleukin-1α and β, interleukin-3, interleukin-4, interleukin-6, interleukin-2, epidermal growth factor (EGF), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cyclosporine, exedine, lanreotide, luteinizing hormone-releasing hormone (LHRH), nafarelin, parathyroid hormone, pramlintide, T-20 (enfuvirtide), thymalfasin, and ziconotide.

The energy may include thermal energy, light energy, electric energy, and the like. For example, in photodynamic therapy, microneedles may be used to direct light to a specific site in the body, so that the light directly acts on a tissue or acts on a mediator such as a light-sensitive molecule.

The drug may be in a variety of states, and may be in a solid or liquid phase, in particular, a powder or highly-concentrated state.

Meanwhile, in a case where the microneedle 200 is a hollow-type microneedle, the solid phase formulation material may be a metallic material or may release a drug through the hollow structure.

Optionally, the microneedle 200 may be loaded with two or more solid phase formulation materials to form a multi-layer structure.

Here, the multi-layer structure may be formed in a state of being divided into an outer layer structure and an inner layer structure, may be formed in a state of being divided into a core layer structure and a shell layer structure, or may be formed in a state of being divided into an upper layer structure and a lower layer (base layer) structure. Here, a solid phase formulation material included in the outer layer structure, the shell layer structure, or the lower layer (base layer) structure is characterized by not only having high reactivity with the liquid-phase formulation material 300 but also having a high solubility in the body, as compared with a solid phase formulation material included in the inner layer structure, the core layer structure, or the upper layer structure.

In particular, in a case where the multi-layer structure is formed in a state of being divided into a core layer structure and a shell layer structure or in a state of being divided into an upper layer structure and a lower layer (base layer) structure, an advantage that the microneedle 200 can be easily removed from the support 100 and easily transferred to the skin is provided by selecting, as a solid-phase formulation material to be contained in the shell layer or lower layer (base layer) structure, a material having a high solubility in the body, which provides an advantage of shortening the time taken for the microneedle 200 to be applied to the body.

FIGS. 4(A) to 4(E) illustrate views showing various structures of microneedles in a microneedle array with a composite formulation according to an embodiment of the present invention.

Figure 4:
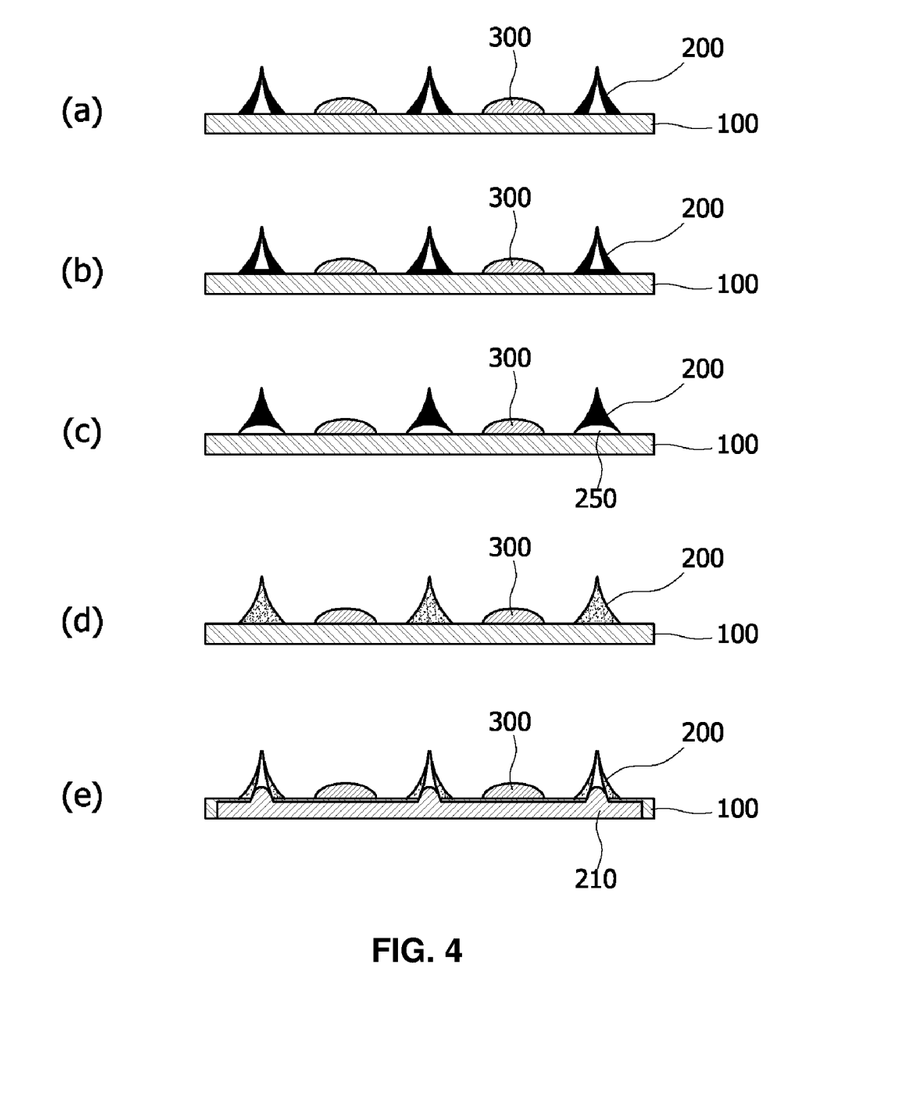
FIG. 4 illustrates views showing various structures of microneedles in a microneedle array with a composite formulation according to an embodiment of the present invention.

As illustrated in FIGS. 4(A) to 4(C), the microneedles 200 may be loaded with two or more solid-phase formulation materials to form multi-layer structures [outer layer-inner layer structure, core layer-shell layer structure, and upper layer-lower layer (base layer) structure]. As illustrated in FIG. 4(D), the microneedle 200 is a solid-type microneedle and may be loaded with a metallic material as the solid-state pharmaceutical material. As illustrated in FIG. 4(E), the microneedle 200 is a hollow-type microneedle and may be loaded with a metallic material as the solid-state pharmaceutical material, in which a drug 210 may be released through the hollow structure.

Next, the microneedle array with a composite formulation according to the present invention contains a liquid-phase formulation material 300, and is characterized in that the liquid-phase formulation material 300 is applied or added dropwise onto an area of the upper portion of the support 100 in which the microneedle 200 is not formed. Alternatively, the microneedle array is characterized in that the liquid-phase formulation material 300 is released, through one or more holes 150 formed in the support 100, onto an area of the upper portion of the support 100 in which the microneedle 200 is not formed.

Thus, the liquid-phase formulation material 300 can be delivered into the body (transdermally, mucosally, or the like), simultaneously with the solid-phase formulation material loaded on the microneedle 200, thereby serving to diversify efficacy; and, in addition, the liquid-phase formulation material 300 can interact with the solid-phase formulation material loaded on the microneedle 200 to regulate a rate at which the microneedle 200 is dissolved in the body, thereby serving to maximize efficacy. In addition, the liquid-phase formulation material 300 may have, by nature, adhesive strength of a predetermined magnitude, thereby serving to adhere the microneedle array to the human body.

Specifically, the microneedle array is characterized in that the liquid-phase formulation material 200 may be entirely or partially applied or added dropwise onto an area of the upper portion of the support 100 in which the microneedle 200 is not formed. However, a part of the liquid-phase formulation material 200 may be entirely or partially applied or added dropwise onto even an area of the upper portion of the support 100 in which the microneedle 200 is formed.

FIGS. 5(A) to 5(D) illustrate views showing various application positions of a liquid-phase formulation material in a microneedle array with a composite formulation according to an embodiment of the present invention.

Figure 5:
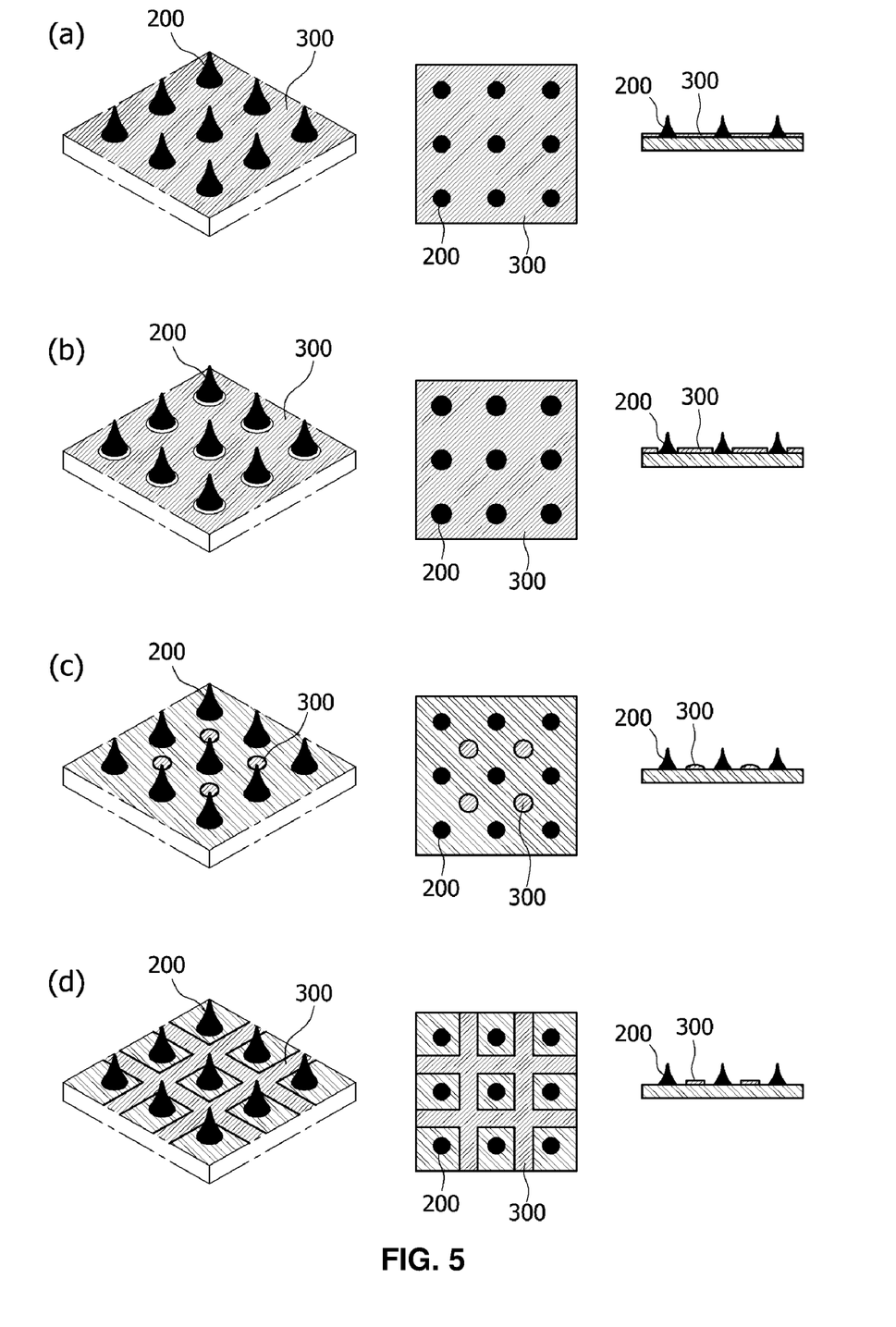
FIG. 5 illustrates views showing various application positions of a liquid-phase formulation material in a microneedle array with a composite formulation according to an embodiment of the present invention.

As illustrated in FIGS. 5(A), 5(B), and 5(D), the liquid-phase formulation material 300 may be entirely or partially applied onto an area of the upper portion of the support 100 in which the microneedle 200 is not formed. As illustrated in FIG. 5(C), the liquid-phase formulation material 300 may be partially added dropwise onto an area of the upper portion of the support 100 in which the microneedle 200 is not formed. Through this patterning, a degree of interaction between the solid phase formulation material loaded on the microneedle 200 and the liquid formulation material 300 can be regulated.

Alternatively, the microneedle array is characterized in that the liquid-phase formulation material 300 is released, through one or more holes 150 formed in the support 100, onto an area of the upper portion of the support 100 in which the microneedle 200 is not formed. In a case where the support 100 has a plate structure and has one or more holes 150 formed entirely through the support 100, the liquid-phase formulation material 300 is in a state of being injected to be positioned in the lower portion of the support 100. On the other hand, in a case where the support 100 has a polyhedral structure having one or more inner hollow spaces and has one or more holes 150 formed entirely through the upper surface of the support 100, the liquid-phase formulation material 300 is in a state of being injected to be positioned in the inside of the support 100.

In addition, a type of the liquid-phase formulation material 300 may be the same as or different from that of the solid formulation material.

In a case where the type of the liquid-phase formulation material 300 is the same as that of the solid-phase formulation material, the liquid-phase formulation material 300 may be a biocompatible or biodegradable material. Specific types of the biocompatible or biodegradable material are as mentioned above, and thus redundant description will be omitted.

In a case where the type of the liquid-phase formulation material 300 is different from that of the solid formulation material, in an example, the liquid-phase formulation material 300 can contain a material which is difficult to be loaded on a viscous composition for forming the microneedle 200 in a case where the viscous composition is molded and cured to form the microneedle 200, which provides an advantage that such a material can also be effectively delivered into the body. More specifically, the liquid-phase formulation material 300 may contain a fat-soluble material including one or more selected from the group consisting of horse oil, vitamin A and a derivative thereof, vitamin D and a derivative thereof, vitamin E and a derivative thereof, vitamin K and a derivative thereof, organic sunscreen, and a fat-soluble plant extract; or a water-soluble material including one or more selected from the group consisting of vitamin B and a derivative thereof, vitamin C and a derivative thereof, epigallocatechin gallate, a water-soluble plant extract, a water-soluble flavor, an enzyme, a microbial extract, and a mineral. The liquid-phase formulation material 300 preferably contains, but is not limited to, a fat-soluble material which is particularly difficult to be loaded on the viscous composition for forming the microneedle 200.

In another example, the liquid-phase formulation material may contain a material for dissolving the microneedles, which provides an advantage that a dissolution rate of the solid-phase formulation material loaded on the microneedle 200 can be regulated to be fast when the microneedles 200 are applied to the human body. More specifically, the liquid-phase formulation material 300 may be selected from the group consisting of water, C1 to C4 anhydrous or anhydrous lower alcohol, benzene, toluene, xylene, hexane, chloroform, ether, acetone, and amine, with water, lower alcohol, and the like being preferred. However, the present invention is not limited thereto.

In yet another example, the liquid-phase formulation material 300 has an advantage that it may contain a material for protecting the skin from the microneedles 200 when the microneedles 200 are applied to the human body. More specifically, the liquid-phase formulation material 300 may contain a humectant, a skin cleanser, a disinfectant, a skin-restoring agent, a sedative, and the like. Examples of the humectant may include glycerin, propylene glycol, sorbitol, amino acid, butylene glycol, and hyaluronic acid. Examples of the skin cleansing agent may include various polymer compounds, polyol, ester oil, oil and fat, a silicone compound, and the like. The disinfectant may include C1 to C4 lower alcohol, salicylic acid, camphor, and the like. The skin-restoring agent may include ceramide, almond, Argan vegetable oil, shea butter, and the like.

In addition, the liquid-phase formulation material 300 may also further contain a drug. Specific types of the drug are also as mentioned above, and thus redundant description will be omitted.

Meanwhile, the liquid-phase formulation material 300 may form a multi-layer structure. In an example, the liquid-phase formulation material 300 may form a multi-layer structure in a state of being divided into an upper layer structure and a lower layer structure. The liquid-phase formulation material 300 included in the upper layer structure is a material which reacts first with the solid-phase formulation material loaded on the microneedle 200 and which can, for example, serve to disinfect the skin. In addition, the liquid-phase formulation material 300 included in the lower layer structure is a material which reacts later with the solid-phase formulation material loaded on the microneedle 200 and which can, for example, serve to restore the skin.

In addition, the liquid-phase formulation material 300 may be encapsulated. A membrane 350 for encapsulating the liquid-phase formulation material may also be a biocompatible or biodegradable material. Specific types of the membrane 350 are as mentioned above, and thus redundant description will be omitted.

Such encapsulation has advantages in that it allows the liquid-phase formulation material 300 to provide protection from an external environment, maintenance, and a buffering action during storage, and allows the liquid-phase formulation agent 300 contained in the membrane to be smoothly released under a certain condition at the time of being applied to the human body.

Figure 6:
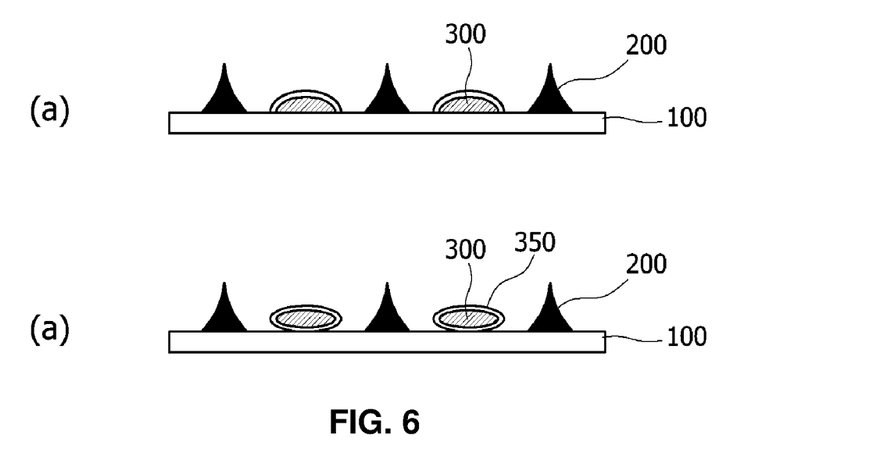
FIG. 6 illustrates views showing various structures of a liquid-phase formulation material in a microneedle array with a composite formulation according to an embodiment of the present invention.

FIGS. 6(A) and 6(B) illustrate views showing various structures of a liquid-phase formulation material in a microneedle array with a composite formulation according to an embodiment of the present invention.

As illustrated in FIG. 6(A), the liquid-phase formulation material 300 may form a multi-layer structure in a state of being divided into an upper layer structure and a lower layer structure. As illustrated in FIG. 6(B), the liquid-phase formulation material 300 may be encapsulated by a membrane 350.

Optionally, pressurizing means 400 for releasing the liquid-phase formulation material may be included, and a trigger, a syringe, or the like may be used as the pressurizing means 400. For example, in a case where the support 100 has a flexible polyhedral structure having one or more inner hollow spaces and the liquid formulating material 300 is injected into the inside of the support 100, the liquid formulating material 300 may be released by pressing the lower portion of the support 100.

Optionally, the adhesive layer (not shown) may be formed on the lower portion of the support 100, and the adhesive layer (not shown) may be formed larger than the area of the support 100 so as to be attached to the human body. Specifically, the adhesive layer (not shown) may be formed to include a pressure sensitive adhesive so as to be easily attached to a human body. Here, for the adhesive, it is preferable to use silicones such as polydimethylsiloxane, an acrylic adhesive such as polyacrylate, a polyisobutylene-based adhesive, and the like. However, the adhesive is not limited thereto.

Method (1) for Manufacturing Microneedle Array

In an embodiment of the present invention, there is provided a method for manufacturing a microneedle array, comprising: (a) a step of preparing a support; (b) a step of forming, on the upper portion of the support, a plurality of microneedles loaded with a solid-phase formulation material which protrude from the upper portion; and (c) a step of applying or adding dropwise a liquid-phase formulation material onto an area of the upper portion of the support in which the microneedle is not formed.

The "support", "plurality of microneedles loaded with a solid-phase formulation material", and "liquid-phase formulation material" constituting the microneedle array according to another embodiment of the present invention have been described above, and thus redundant description will be omitted.

First, the method for manufacturing a microneedle array according to the embodiment of the present invention comprises the step [step (a)] of preparing a support.

Next, the method comprises the step [step (b)] of forming, on the upper portion of the support, a plurality of microneedles loaded with a solid-phase formulation material which protrude from the upper portion.

Specifically, the microneedles may be obtained by placing a plurality of viscous compositions on the upper portion of the support, and performing molding and curing thereof. Here, the molding may be performed by applying an outward force to the viscous compositions, or may be performed by micromolding or 3D printing.

More specifically, in a case where the microneedles are formed by applying an outward force to the viscous compositions, the microneedles may be formed according to the following method.

The first method is a method (drawing lithography method) described in Korean Patent No. 0793615 which has been developed by the present inventors.

The second method is a method (centrifugal force method) described in Korean Patent Application No. 2013-0050462 which has been developed by the present inventor.

The third method is a method (negative pressure method) described in Korean Patent No. 10-1488397 which has been developed by the present inventor.

The fourth method is a method (manufacturing method for microstructures by CCDP method) described in Korean Patent Application No. 2015-0072107 which has been developed by the present inventor.

The fifth method is a method (manufacturing method for solid microstructures by blowing) described in Korean Patent No. 10-1136738 which has been developed by the present inventor.

Each of these techniques is one embodiment implemented by the present inventors, among manufacturing methods for inserting microneedles into the body.

Next, the method for manufacturing a microneedle array according to the embodiment of the present invention comprises the step [step (c)] of applying or adding dropwise a liquid-phase formulation material onto an area of the upper portion of the support in which the microneedle is not formed.

Specifically, the application or dropwise addition may be carried out by a known method. Here, the application may be carried out by spraying, vapor deposition, electrospinning, or the like, and the dropwise addition may be carried out by ejection using a dispenser.

The step (c) may be performed after the step (b), and the step (c) may be performed before the step (b).

Optionally, in the method for manufacturing a microneedle array according to the embodiment of the present invention, an adhesive layer may be further bound to the lower portion of the support.

Method (2) for Manufacturing Microneedle Array

In another embodiment of the present invention, there is provided a method for manufacturing a microneedle array, comprising: (a) a step of preparing a support having one or more holes formed therein; (b) a step of forming, on the upper portion of the support, a plurality of microneedles loaded with a solid-phase formulation material which protrude from the upper portion; and (c) a step of releasing a liquid-phase formulation material, through the holes, onto an area of the upper portion of the support in which the microneedle is not formed.

The "support having one or more holes formed therein", "plurality of microneedles on which a solid-phase formulation material is loaded", and "liquid-phase formulation material" constituting the microneedle array according to another embodiment of the present invention have been described above, and thus redundant description will be omitted.

First, the method for manufacturing a microneedle array according to the other embodiment of the present invention comprises the step [step (a)] of preparing a support having one or more holes formed therein.

Next, the method comprises the step [step (b)] of forming, on the upper portion of the support, a plurality of microneedles loaded with a solid-phase formulation material which protrude from the upper portion.

Specifically, the microneedles may be obtained by placing a plurality of viscous compositions on the upper portion of the support, and performing molding and curing thereof. Here, the molding method has been described above, and thus redundant description will be omitted.

The method may further comprise, before or after formation of the microneedles, a step of injecting the liquid-phase formulation material so as to be positioned in the lower portion or the inside of the support.

Specifically, in a case where the support has a plate structure and has one or more holes formed entirely through the support, in order to inject the liquid-phase formulation material into the lower portion of the support, the injection may be carried out, through one or more holes formed in the support, from the upper portion of the support, or may be carried out from the lower portion of the support.

On the other hand, in a case where the support 100 has a polyhedral structure having one or more inner hollow spaces and has one or more holes formed entirely through the upper surface of the support, in order to inject the liquid-phase formulation material into the inside of the support, the injection may be carried out, through one or more holes formed in the upper surface of the support, from the upper portion of the support.

In addition, the injection may be carried out by a known method. Here, the injection may be carried out by spraying, vapor deposition, electrospinning, ejection using a dispenser, or the like.

Next, the method for manufacturing a microneedle array according to the other embodiment of the present invention comprises the step [step (c)] of releasing a liquid-phase formulation material, through the holes, onto an area of the upper portion of the support in which the microneedle is not formed.

Specifically, pressurizing means may be used to release the liquid-phase formulation material, and a trigger, a syringe, or the like may be used as the pressurizing means.

The step (c) may be performed after the step (b), and the step (c) may be performed before the step (b).

Optionally, in the method for manufacturing a microneedle array according to the other embodiment of the present invention, an adhesive layer may be further bound to the lower portion of the support.

Hereinafter, the present invention will be described in more detail by way of examples. These examples are provided only to more specifically describe the present invention, and it will be apparent to those skilled in the art that the scope of the present invention is not limited by these examples, in accordance with the gist of the present invention.

EXAMPLES

Example 1

Figure 7:
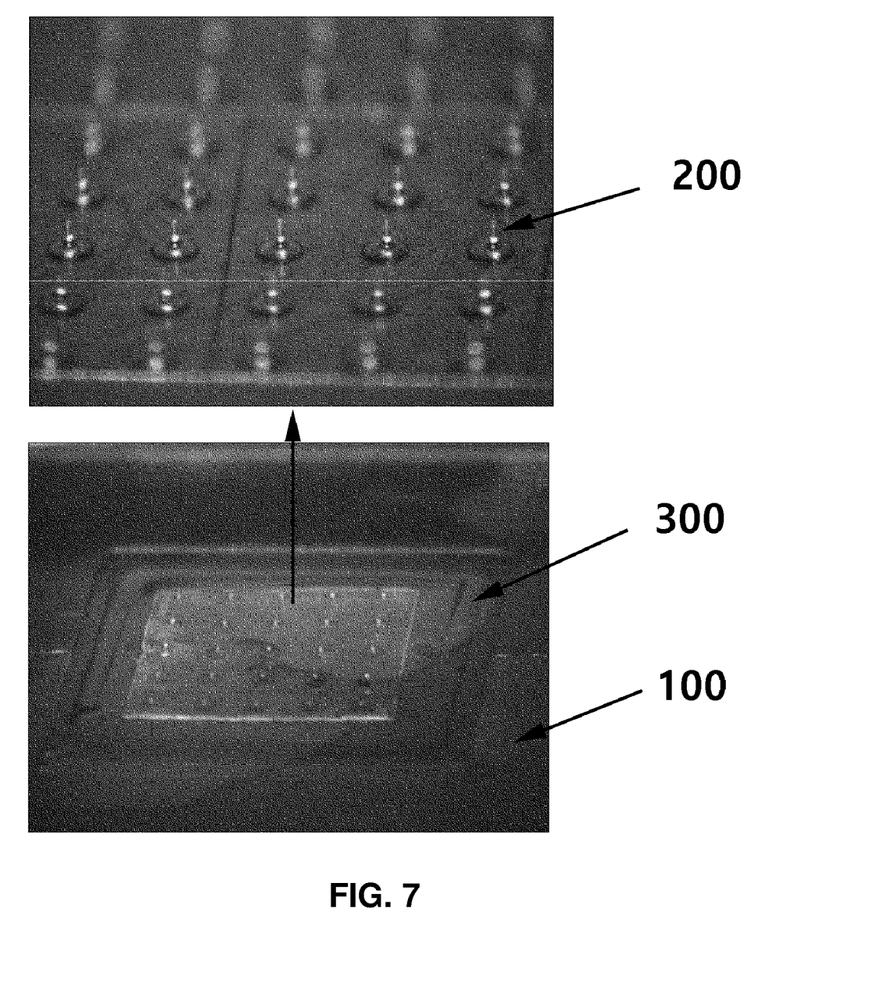
FIG. 7 illustrates photographs showing a microneedle array manufactured according to Example 1.

A first support formed of carboxymethyl cellulose (CMC) material was prepared, and then an aqueous solution of 65% (w/v) hyaluronic acid and 0.7% (w/v) adenosine was added dropwise onto the upper portion of the support at 0.9 kgfcm$^{-1}$ for one minute through a dispenser (ML-5000X; Musashi Engineering, Inc., Japan), to form a viscous composition array having a plurality of droplet shapes loaded with an adenosine drug. Then, the first support was assembled with a second support formed of CMC material, and centrifugal force of 2,500 rpm was applied thereto for 1 minute. During this process, a plurality of hourglass-shaped microstructures were formed between the two supports through molding and curing using centrifugal force, and then the two supports were separated to produce a plurality of microneedles (effective length=about 250 mm, tip diameter of pointed portion=about 25 μm, and bottom diameter of pointed portion=about 500 μm). Then, horse oil was applied, through a dispenser (ML-5000X; Musashi Engineering, Inc., Japan), to the entire edge area of the upper portion of the support in which the microneedle is not formed, so that a microneedle array was finally manufactured (see FIG. 7). Here, it was identified that a content of hyaluronic acid is 0.41 mg, a content of adenosine is 0.004 mg, and a content of horse oil is 1.13 mg, per finally manufactured microneedle array.

Example 2

Figure 8:
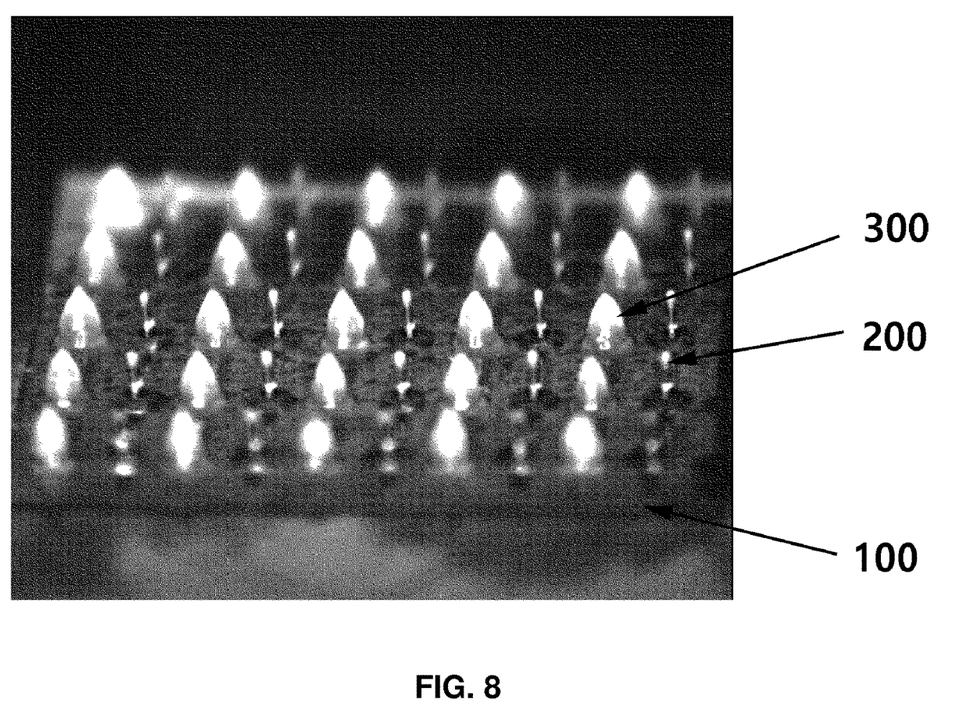
FIG. 8 illustrates a photograph showing a microneedle array manufactured according to Example 2.

A first support formed of carboxymethyl cellulose (CMC) material was prepared, and then an aqueous solution of 65% (w/v) hyaluronic acid and 0.7% (w/v) adenosine was added dropwise onto the upper portion of the support at 0.9 kgfcm$^{-1}$ for one minute through a dispenser (ML-5000X; Musashi Engineering, Inc., Japan), to form a viscous composition array having a plurality of droplet shapes loaded with an adenosine drug. Then, the first support was assembled with a second support formed of CMC material, and centrifugal force of 2,500 rpm was applied thereto for 1 minute. During this process, a plurality of hourglass-shaped microstructures were formed between the two supports through molding and curing using centrifugal force, and then the two supports were separated to produce a plurality of microneedles (effective length=about 350 mm, tip diameter of pointed portion=about 25 μm, and bottom diameter of pointed portion=about 500 μm). Then, droplet-shaped serum [composition: Ceramide 27.2%, Biocare R 20%, Steric acid 16.3%, Lanette O 2.7%, and Meadow Foam Seed Oil 33.3%] was added dropwise onto an area of the upper portion of the support in which the microneedle is not formed, between the microneedles, at 0.9 kgfcm$^{-1}$ for one minute through a dispenser (ML-5000X; Musashi Engineering, Inc., Japan), so that a microneedle array was finally manufactured (see FIG. 8). Here, it was identified that a content of hyaluronic acid is 0.41 mg and a content of adenosine is 0.004 mg, per finally manufactured microneedle array.

The foregoing description of the present invention is provided for illustration. It will be understood by those skilled in the art that various changes and modifications can be easily made without departing from the technical spirit or essential features of the present invention. Therefore, it is to be understood that the above-described examples are illustrative in all aspects and not restrictive.

The invnetion claimed is:

1. A microneedle array, comprising:
   a support; and
   a plurality of microneedles loaded with a solid-phase formulation material which protrude from an upper portion of the support, wherein the support and the plurality of microneedles are made of different material and the plurality of microneedles are dissolvable in a body of a subject,
   wherein a liquid-phase formulation material is applied or added dropwise onto an area of the upper portion of the support in which the plurality of microneedles are not formed, or in a case where one or more holes are formed in the support, the liquid-phase formulation material is released, through the holes, onto the area of the upper portion of the support in which the microneedle is not formed.

2. The microneedle array according to claim 1, wherein the plurality of microneedles are loaded with two or more solid-phase forming materials to form a multi-layer structure.

3. The microneedle array according to claim 1, wherein a type of the liquid-phase formulation material is the same as or different from that of the solid-phase formulation material.

4. The microneedle array according to claim 3, wherein in a case where the type of the liquid-phase formulation material is different from that of the solid-phase formulation material, the liquid-phase formulation material contains a fat-soluble material including one or more selected from the group consisting of horse oil, vitamin A and a derivative thereof, vitamin D and a derivative thereof, vitamin E and a derivative thereof, vitamin K and a derivative thereof, organic sunscreen, and a fat-soluble plant extract; or a water-soluble material including one or more selected from the group consisting of vitamin B and a derivative thereof, vitamin C and a derivative thereof, epigallocatechin gallate, a water-soluble plant extract, a water-soluble flavor, an enzyme, a microbial extract, and a mineral.

5. The microneedle array according to claim 3, wherein in a case where the type of the liquid-phase formulation material is different from that of the solid-phase formulation material, the liquid-phase formulation material contains a material for dissolving the microneedles when the microneedles are applied to the body.

6. The microneedle array according to claim 3, wherein in a case where the type of the liquid-phase formulation material is different from that of the solid-phase formulation material, the liquid-phase formulation material contains a material for protecting the skin from the microneedles when the microneedles are applied to the body.

7. The microneedle array according to claim 1, wherein the liquid-phase formulation material is encapsulated.

8. The microneedle array according to claim 1, further comprising:
a pressurizing means for releasing the liquid-phase formulation material.

9. The microneedle array according to claim 1, further comprising:
an adhesive layer formed on a lower portion of the support.

10. A method for manufacturing a microneedle array, comprising:
(a) a step of preparing a support;
(b) a step of forming, on an upper portion of the support, a plurality of microneedles loaded with a solid-phase formulation material which protrude from the upper portion, by placing a plurality of viscous compositions on the upper portion of the support, and then performing molding and curing thereof to form, wherein the support and the plurality of microneedles are made of different material; and
(c) a step of applying or adding dropwise a liquid-phase formulation material comprising a material for dissolving the plurality of microneedles onto an area of the upper portion of the support in which the plurality of microneedles are not formed.

11. A method for manufacturing a microneedle array, comprising:
(a) a step of preparing a support having one or more holes formed therein;
(b) a step of forming, on an upper portion of the support, a plurality of microneedles loaded with a solid-phase formulation material which protrude from the upper portion, by placing a plurality of viscous compositions on the upper portion of the support, and then performing molding and curing thereof to form, wherein the support and the plurality of microneedles are made of different material; and
(c) a step of releasing a liquid-phase formulation material comprising a material for dissolving the plurality of microneedles, through the holes, onto an area of the upper portion of the support in which the plurality of microneedles are not formed.

12. The method according to claim 11, further comprising, before or after the step (b):
a step of injecting the liquid-phase formulation material so as to be positioned in a lower portion or an inside of the support.

* * * * *